United States Patent [19]

Chen

[11] Patent Number: 4,727,126
[45] Date of Patent: Feb. 23, 1988

[54] NOVEL DIOL MONOMERS AND POLYMERS THEREOF

[75] Inventor: Tsang J. Chen, Rochester, N.Y.

[73] Assignee: Eastman Kodak Company, Rochester, N.Y.

[21] Appl. No.: 926,750

[22] Filed: Nov. 4, 1986

Related U.S. Application Data

[63] Continuation-in-part of Ser. No. 857,287, Apr. 30, 1986, abandoned.

[51] Int. Cl.$^4$ ............................................. C08F 26/02
[52] U.S. Cl. ...................................... 526/302; 528/75; 528/291; 528/367; 564/60
[58] Field of Search .................. 526/302; 528/75, 291, 528/367; 564/60

[56] References Cited

U.S. PATENT DOCUMENTS 4,320,221  3/1982  Hoffman .............................. 528/69

Primary Examiner—Maurice J. Welsh
Attorney, Agent, or Firm—John R. Everett

[57] ABSTRACT

Compounds are disclosed having the structure

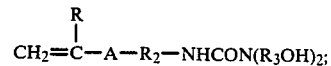

wherein
A represents arylene or carboxyl;
R represents H or CH$_3$; and
R$_2$ and R$_3$, each independently, represents alkylene of 2 to 7 carbon atoms.

The compounds are useful in making curable polyurethane, polyesters and vinyl polymers.

17 Claims, No Drawings

NOVEL DIOL MONOMERS AND POLYMERS THEREOF

This is a continuation-in-part of my earlier filed application Ser. No. 857,287, filed on Apr. 30, 1986 and now abandoned.

FIELD OF THE INVENTION

This invention relates to new diols, the method of making such diols and curable polyurethanes, polyesters and vinyl polymers made from such diols.

BACKGROUND OF THE INVENTION

Polyurethanes that are curable by exposure to electron beams are usually prepared by end capping and isocyanate group of the desired polyurethane prepolymer with hydroxy-containing acrylate and methacrylate monomers. However, pendant, unsaturated groups cannot be inserted into the polymer chain using this approach.

Glyceryl allyl ether is a commercially available unsaturated diol which is used to insert unsaturated groups randomly into a polyurethane chain. However, the reactivity of the allyl group is less than desirable and the curing of the resulting polyurethane polymer is often sluggish. No other diols with more active functional groups such as acrylate, methacrylate or vinyl diols have been disclosed. There is a clear need for a means of inserting more active unsaturated groups randomly and at any desired level into urethane polymers. Such polymers could be more readily cured by high-energy e-beam radiation or with conventional free-radical initiators than those which include less active randomly inserted groups from glyceryl allyl ether.

U.S. Pat. No. 4,320,221 discloses a method for making curable adhesive compositions wherein the uncured composition comprises monomers or macromers, end capped with unsaturated methacrylate groups. In particular, this patent discloses the reaction of an isocyanatoethyl acrylate, particularly 2-isocyanatoethyl methacrylate with a polyahl such as diethanolamine in the presence of dibutyl-tin-dilaurate at temperatures of 70° C. and above to form the monomers or macromers which are end capped with unsaturated methacrylate functional groups. Under the conditions of the reaction, all —OH, =NH or NH$_2$ groups are reacted with the isocyanatoethyl methacrylate to form unsaturated methacrylate end capped monomers. Such monomers are useful as adhesives, but are not useful for inserting unsaturated groups ran-domly and at any desired level into polymer chains, particularly polyurethane polymers.

SUMMARY OF THE INVENTION

The present invention provides diol monomers which can be used to make polyurethanes, polyesters, polycarbonates and vinyl polymers. The polymers are e-beam, free-radical, or heat curable. The novel diol monomers can be used to insert unsaturated groups into the chain of such polymers randomly and at any desired level.

The diol monomers of this invention are compounds having the structure:

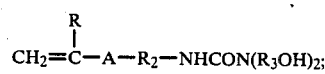

wherein
A represents arylene or carboxyl;
R represents H or CH$_3$; and
R$_2$ and R$_3$, each independently, represents alkylene of 2 to 7 carbon atoms.

The monomers of this invention are made by reacting an isocyanatoalkyl acrylate or an isocyanotoarylvinyl with a dialkanolamine, at a temperature of 10° to 35° C., in (a) an inert atmosphere (b) the presence of a free-radical inhibitor and (c) a urethane catalyst.

The reaction, carried out according to the method of this invention, selectively involves only one active hydrogen group. This preserves the two hydroxyl groups of the dialkanol amine reactant. Hence, the monomer produced by the method of the present invention is different from the monomer provided by the method used in U.S. Pat. No. 4,320,221 wherein all of the hydroxyl and active hydrogen groups are involved in the reaction between the isocyanatoalkyl acrylate and the dialkanol amine.

PREFERRED EMBODIMENTS OF THE INVENTION

Preferred diol monomers of this invention have the structure

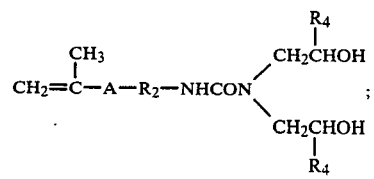

wherein
A represents carboxyl or phenylene;
R$_2$ represents ethylene or isopropylene; and
R$_4$ represents H or CH$_3$.

DETAILS OF THE INVENTION

As stated before, the diol monomers of this invention are made by reacting an isocyanatoalkylacrylate or an isocyanatoarylvinyl with a dialkanol amine at a temperature of 10° to 35° C., in (a) an inert atmosphere (b) the presence of a free-radical inhibitor and (c) the presence of a urethane catalyst.

All the starting materials used in this method are readily available or can be easily made by procedures well known to those skilled in this art.

Useful isocyanatoalkyl acrylates include 2-isocyanatoethyl methacrylate (IEM) and 2-isocyanatoethyl acrylate.

A useful isocyanoto arylvinyl is α,α-dimethylmeta-isopropenyl benzy isocyanate (available from American Cyanamid Co.).

Useful dialkanolamines include diethanolamine, diisopropanol amine and di-sec-butanol amine.

Free-radical inhibitors function in the reaction to preserve acrylate or methacrylate groups by preventing unwanted polymerization of the acrylic groups. Useful free-radical inhibitors include methylhydroquinone (Me-Mq), hydroquinone and p-methoxyphenol.

Urethane catalysts are used in the reaction to promote low temperature reactions. Such catalysts include dibutylin dilaurate (DBTDL), dibutyl tin diacetate and stannous dioctoate.

The reaction is carried out under an inert atmosphere to protect the unsaturated groups. Such inert atmospheres can be provided with nitrogen (N₂), or argon (Ar).

The diols of this invention are prepared in accordance with the following reaction scheme. The preparation of the novel diol monomer of this invention, 2-N',N'-[bis(2-hydroxyethyl)ureido]ethyl methacrylate is illustrated.

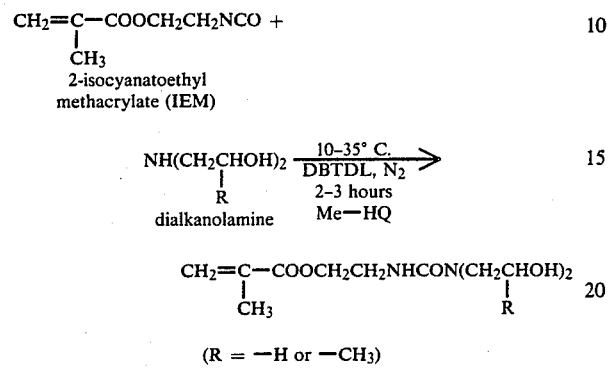

(R = —H or —CH₃)

No solvent is needed to prepare these new diols and the yield is quantitative as shown by NMR spectra. The reaction of —NCO with the —NH group is not interfered with even in the presence of H₂O or CH₃OH.

The following example specifically illustrates the preparation of diol monomers according to the foregoing reaction scheme.

EXAMPLE 1

Preparation of 2-[N',N'-Bis(2-hydroxyethyl)ureido]ethyl Methacrylate

A one liter flask, under a N₂ blanket, was charged with 105 gm of diethanolamine (1 mole) and 20 mg of methylhydroquinone. One molar of 2-isocyanatoethyl methacrylate (IEM) containing 2 ml of DBTDL (2% solution in toluene) was dropped slowly in the flask with moderate stirring over a period of 105 minutes, while the temperature was maintained at 20° to 25° C. with an ice-bath. The resulting viscous solution was stirred for an additional 60 minutes at 20° C. and then discharged. The product showed no NCO absorption in the IR spectrum and the NMR spectrum was consistent with the proposed structure. Gas chromatography also indicated the purity of the product to be greater than 95%. Additional inhibitor was added (to a total of 250 ppm) and the diol was stored in a freezer.

Anal. Calc'd. for C₁₁H₂₀N₂O₅: C, 50.8; H, 7.7; N, 10.8. Found: C, 50.6; H, 7.5; N, 10.7.

EXAMPLE 2

Preparation of 2-[N',N'-Bis(1-hydroxy-2-propyl)ureido]ethyl Methacrylate

A 1-liter flask under a N₂ blanket was charged with 1 mole (133 gm) of diisopropanolamine and 72 mg of p-methoxyphenol. One mole (155 gm) of IEM containing 2 ml of 2% DBTDL was slowly dropped in the flask under moderate stirring over a period of 150 minutes while maintaining the temperature at 30° C. Stirring continued for an additional 90 minutes at 35° C. and the product was discharged. The IR spectrum showed no NCO absorption and NMR spectrum was consistent with the proposed structure.

Anal. Calc'd. for C₁₂H₂₂N₂O₅: C, 54.2; H, 8.4; N, 9.7. Found: C, 54.4; H, 8.1; N, 10.0.

Polyurethane may be prepared from the acrylate diols of this invention using known methods in which an isocyanate comonomer is reacted with a diol. Such methods are described in *Preparative Methods of Polymer Chemistry*, by Sorenson and Campbell, pp. 126-128. Other diols may be used in this reaction other than the acrylate diols of this invention. In order to achieve reasonable curable rates, from 0.5 to 50 mole percent, preferably from 0.5 to 20 mole percent, recurring diol derived units should be derived from the acrylate diols of this invention, based on the total diols used in making the polyurethane.

Examples 3-7 and Table I infra, illustrate the range of polyurethanes which can be made using the acrylate diols of this invention as well as the fact that such polyurethanes are free-radical or e-beam curable.

EXAMPLE 3

Preparation of an E-Beam Curable Polyurethane (Polymer 1, Table I)

A 2-liter flask was charged with 83 gm of a polycaprolactone diol (MW 830) supplied by Union Carbide), and 26 gm of the methacrylate diol (MW 260) prepared according to Example 1. The polycaprolactone diol has the structure

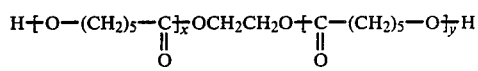

x+y in combination are sufficient to give a MW of 830.

The contents were heated to 30° under a N₂ blanket. A solution consisting of 131 gm of methylenedicyclohexyl diisocyanate (RMDI), 4 ml of 2% DBTDL in toluene and 250 gm of tetrahydrofuran (THF) was dropped in the flask over a period of 25 minutes. The temperature was raised to 50°-55° C. The stirring continued for 4 hours. Then 0.31M (27.9 gm) of 1,4-butanediol, dissolved in 150 gm of THF, was added over a 20 minute period. The temperature was adjusted to 60°-65° C. The reaction was continued until no NCO absorption was observed in the IR spectrum. The resulting viscous polyurethane solution was cooled to ambient temperature. Fifty mg of p-methoxyphenol were added as inhibitor. Total solid content was 39.7%.

The polyurethane was diluted to 19.4% with THF. Hand coatings were made on clear poly(ethylene terephthalate) support. The coatings were then cured by irradiation with an electron beam in the dose range of 1 Mrad to 10 Mrad. All coatings were found to be crosslinked. They all became insoluble in THF. The Tg increased from about 34° C. to 51° C. as the total radiation dose increased.

Curing of the polyurethane was also accomplished by adding 2,2'-azobis(2-methylpropionitrile) (AIBN) (1 to 4% by weight based on dry polymer) to the above coating solutions and drying the coatings under a N₂ atmosphere. The film also became insoluble in THF or DMF (dimethylformamide).

EXAMPLE 4

Preparation of Polyurethane (Polymer 2, Table I)

Using the procedures similar to Example 3, 130 gm of RMDI, 4 ml of 2% DBTDL and 250 gm of THF were charged into a 2-liter flask. The contents were maintained at 30° C. while a solution of 83 gm of the polycaprolactone diol used in Example 3 dissolved in 100 gm THF was added dropwise over a 20 minute period. The temperature was raised to 60° C. Stirring was continued for 3 hours. A solution comprising 32.3 gm of neopentyl glycol (0.31M), 26 gm of the monomer of Example 1, (0.1M) and 100 gm of THF was then added over a period of 20 minutes. The reaction was continued at 60° C. for 2 hours. An additional 4 ml of 2% DBTDL were added. The stirring was continued until no NCO was observed in the IR spectrum. The contents were then cooled to room temperature. Methylhydroquinone (54.3 mg) were added as inhibitor (200 ppm). The total solids was found to be 39.6%. The polymer was curable either by electron beam or by AIBN, as described in Example 3.

EXAMPLES 5, 6 AND 7

Preparation of Polymers 3, 4 and 5 of Table I

Additional e-beam or free-radical curable polyurethanes were prepared according to the procedures of the above examples. See polymers 3, 4 and 5 of Table I for structures. All showed good response to e-beam and AIBN curing.

Polyesters comprising recurring units derived from the acrylate diols of this invention are made using well known methods for making polyesters. Such methods are disclosed in *Preparative Methods of Polymer Chemistry*, by Sorenson and Campbell, pp. 137–144. The acrylate diols of this invention are used along with other selected diols to make the final polyesters. To insure that the resulting polyesters are e-beam and free-radical curable, from 0.5 to 50 mole percent, preferably from 0.5 to 20 mole percent of the total diol derived recurring units should be derived from the acrylate diols of this invention.

Example 8 illustrates a method for using the acrylate diols of this invention to make polyesters. Example 8 also illustrates that the polyesters are free-radical curable and thus, usable in any situation in which curable polyesters are desired.

EXAMPLE 8

Preparation of a Polyester (Polymer 6, Table I)

A high Tg, curable polyester was prepared by incorporating the monomer of Example 1 into the polyester using the following method.

A 1-liter flask, under $N_2$, was charged with 0.1 mole of terephthaloyl chloride (20.3 gm) and 100 gm of THF. The temperature was maintained at 15°–20° C. A solution of 0.08 mole 4,4'-(hexahydro-4,7-methanoindan-5-ylidene)bis(phenol) (25.6 gm), 0.02 mole of the monomer of Example 1 (5.2 gm), 0.22 mole of triethylamine (22 gm) and 100 gm of THF was dropped in the flask over a period of 2 hours. Stirring was continued at ambient temperature overnight. The resulting viscous polymer solution was suction-filtered through a glass funnel. The clear filtrate was then poured into a large excess of water to recover the fibrous, white polyester. The polymer was repeatedly washed with fresh water by means of a Waring blender and finally with a small amount of methanol.

The polymer was then dried at 60° C. in a vacuum oven. The yield was 41 gm (94%). The polymer had an IV of 1.10 measured in THF at a concentration of 0.25 gm/dl at 25° C. and Tg of 245° C. A film cast from a 5% polymer solution in THF was found to readily dissolve in THF after drying at 100° C.; however, a separate film cast in the presence of 2% AIBN (based on polymer weight) and dried under similar conditions was found to be insoluble in THF or $CH_2Cl_2$ indicating curing had occurred through the methacrylate groups.

TABLE I

E-Beam and Free-Radical Curable Polyurethanes and Polyesters

Polymer Number 1 (Example 3)

$$\left[\begin{array}{l}\text{—O—R}_1\text{—O—}_{1.0}\\ \text{—O—R}_2\text{—O—}_{1.0}\\ \text{—O—R}_3\text{—O—}_{3.1}\end{array}\right]\left[\begin{array}{l}\text{C—NH—R}_4\text{—NH—C}\\ \parallel\quad\quad\quad\quad\quad\parallel\\ \text{O}\quad\quad\quad\quad\quad\text{O}\end{array}\right]_{5.0}; \text{ wherein}$$

$-R_1-$ is $-(CH_2)_5-C\underset{\parallel}{\overset{}{C}}\underset{O}{\underset{}{}}\!\!\!+\!O(CH_2)_5-C\underset{\parallel}{\overset{}{C}}\underset{O}{\underset{}{}}\!\!\!\!\overline{\jmath}_x OCH_2CH_2O\!\!+\!C\underset{\parallel}{\overset{}{C}}\underset{O}{\underset{}{}}\!\!\!-(CH_2)_5-O\!\!+\!\!\overline{\jmath}_y\,C\underset{\parallel}{\overset{}{C}}\underset{O}{\underset{}{}}\!\!\!+\!CH_2\!\!\!\overline{\jmath}_5$ $-R_2-$ is $-CH_2CH_2-N-CH_2CH_2-$
$\quad\quad\quad\quad\quad\quad\quad\quad\quad\quad\quad|$
$\quad\quad\quad\quad\quad\quad\quad\quad\quad\quad\quad C-NHCH_2CH_2-O-C-C=CH_2$
$\quad\quad\quad\quad\quad\quad\quad\quad\quad\quad\quad\parallel\quad\quad\quad\quad\quad\quad\parallel\,\,\,\,|$
$\quad\quad\quad\quad\quad\quad\quad\quad\quad\quad\quad O\quad\quad\quad\quad\quad\quad\,\,O\,\,CH_3$ $-R_3-$ is $(CH_2)_4$; and $-R_4-$ is ⬡-S-⬡-CH-⬡-S-⬡ .

(numbers indicate ratios in moles)
x and y in combination represent the numbers of each
unit needed to react a desired molecular weight.

TABLE I-continued
E-Beam and Free-Radical Curable Polyurethanes and Polyesters Polymer Number 2 (Example 4)

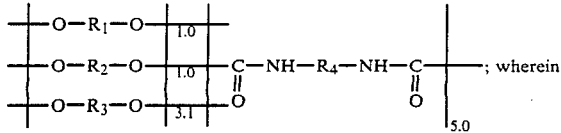

$-R_1-$, $-R_2-$ and $-R_4-$ are the same as Polyurethane Number 1; except

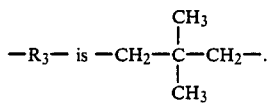

3 (Example 5)

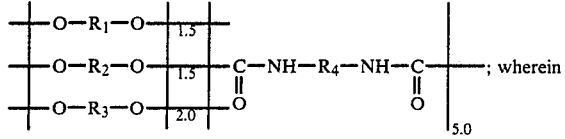

$-R_1-$, $-R_2-$, $-R_3-$ and $-R_4-$ are the same as Polyurethane 2 except mole ratios are different.

4 (Example 6)

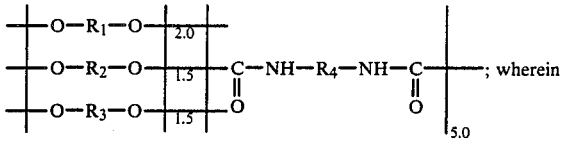

$-R_2-$, $-R_3-$ and $-R_4-$ are the same as Polyurethane 3 except mole ratios are different.
$R_1$ is the polymerized residue of Permapol ™ P-900 poly(thioether) diol sold by Product Research and Chemicals, Inc.

5 (Example 7)

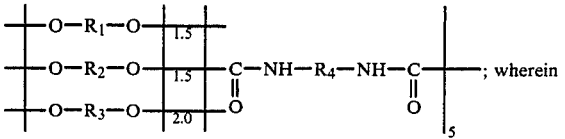

$-R_1-$, $-R_3-$ and $-R_4-$ are the same as Polyurethane 3;

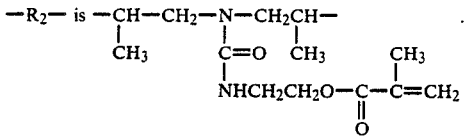

6 (Example 8)

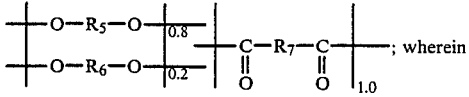

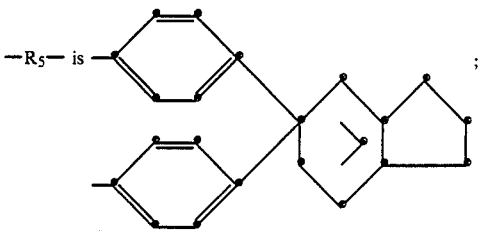

TABLE I-continued
E-Beam and Free-Radical Curable Polyurethanes and Polyesters Polymer Number $-R_6-$ is $-CH_2CH_2\underset{|}{N}-CH_2CH_2-$ ; and
$O=CNHCH_2CH_2\overset{O}{\underset{||}{O}}C-\underset{|}{\overset{CH_3}{C}}=CH_2$ $-R_7-$ is 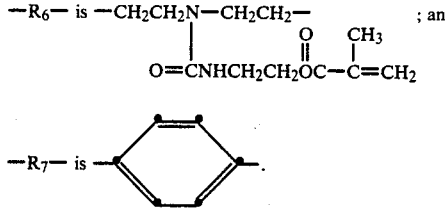

As stated hereinbefore, the acrylate diols of this invention can also be used to make heat curable vinyl, especially acrylic addition polymers for coating applications. Such polymers are made by emulsion, suspension, or solution polymerization.

Examples 9-14 in Table II illustrate the addition-polymerized vinyl polymers which can be made using the novel monomers of this invention. These examples also illustrate that the vinyl polymers made from the acrylate diols of this invention are heat curable. Such vinyl polymers should comprise from 2 to 60 weight percent of units derived from the acrylate diols of this invention to insure curability.

EXAMPLE 9
Polymer 1, Table II

This example illustrates the use of the monomer of Example 1 to prepare a heat-curable acrylate polymer latex for coating applications.

A 1-liter flask, under $N_2$, was charged with 80 gm of $H_2O$ and 0.5 gm (30%) of Triton TM 770 (a surfactant sold by Rohm and Haas Co.). The contents were heated to 70° C. Methyl acrylate (47.5 gm) and the Example 1 monomer (2.5 gm) were combined and emulsified with 70 gm of $H_2O$ and 0.5 gm (30%) of Triton TM 770. Next, 0.2 gm of $Na_2S_2O_5$ was added to the monomer mixture.

An initiation composition of $Na_2S_2O_5$ (0.2 gm) and 0.5 gm of $(NH_4)_2S_2O_8$ were quickly added to the reaction flask and the monomer addition commenced. The addition of monomers was completed in 20 minutes and the reaction was allowed to continue for two more hours at 70° C. It was cooled to ambient temperature to give a good stable latex free from coagulum. Total solid content was 22.6%. A dry film, cast from the latex was found to crosslink after heating at 110° C. for a short period of time. It became insoluble in THF or acetone.

EXAMPLE 10
Polymer 2, Table II

This example describes the preparation of a heat-curable poly(vinyl acetate) latex containing recurring units of the monomer of Example 1.

A 2-liter flask, under $N_2$ was charged with 225 gm of $H_2O$, 40 gm (30%) of Alipal TM E-120 (a surfactant sold by GAF) and 1.25 gm of $NaHCO_3$. The contents were heated to 70° C. Fifteen ml of 5% $K_2S_2O_8$ solution were added. The temperature was raised to 80° C. A monomer mixture comprising 313 gm of vinyl acetate and 17 gm of the Example 1 monomer was slowly dropped in over a six hour period, during which time an additional 35 ml of 5% $K_2S_2O_8$ were also slowly added.

Heating was continued for sixty more minutes at 80°-85° C. Then the contents were cooled to ambient temperature. A latex free from coagulum was obtained.

The solids content was 51.8%. A film cast from the latex after heating at 105°-110° C. was found not soluble in THF.

EXAMPLES 11-14

Additional acrylate latices were prepared according to Example 10, except that the monomer addition was finished within 2 hours. The compositions are shown in Table II. All polymers were found to crosslink after coating as films and heating to 105°-110° C.

TABLE II

| Polymer Number | Vinyl Polymers* |
|---|---|
| 1 (Example 9) | $+CH_2-\underset{\underset{COOCH_3}{\mid}}{CH}\!\!\nearrow_{\!\!95}\!\!-\!\!+CH_2-\underset{\underset{R_1}{\mid}}{\overset{CH_3}{\underset{\mid}{C}}}\!\!\nearrow_{\!\!5}\!;$ wherein<br><br>$R_1$ is $-COOCH_2CH_2NHCON\overset{CH_2CH_2OH}{\underset{CH_2CH_2OH}{<}}$ |
| 2 (Example 10) | $+CH_2-\underset{\underset{\underset{CH_3}{\mid}}{\underset{C=O}{\mid}}{\underset{O}{\mid}}}{CH}\!\!\nearrow_{\!\!95}\!\!-\!\!+CH_2-\underset{\underset{R_1}{\mid}}{\overset{CH_3}{\underset{\mid}{C}}}\!\!\nearrow_{\!\!5}\!;$ wherein<br><br>$R_1$ is $-COOCH_2CH_2NHCON\overset{CH_2CH_2OH}{\underset{CH_2CH_2OH}{<}}$ |
| 3 (Example 11) | $+CH_2-\underset{\underset{COOC_4H_9}{\mid}}{CH}\!\!\nearrow_{\!\!95}\!\!-\!\!+CH_2-\underset{\underset{R_1}{\mid}}{\overset{CH_3}{\underset{\mid}{C}}}\!\!\nearrow_{\!\!5}$<br><br>$R_1$ is $-COOCH_2CH_2NHCON\overset{CH_2CH_2OH}{\underset{CH_2CH_2OH}{<}}$ |
| 4 (Example 12) | $+CH_2-\underset{\underset{COOC_2H_5}{\mid}}{CH}\!\!\nearrow_{\!\!95}\!\!-\!\!+CH_2-\underset{\underset{R_1}{\mid}}{\overset{CH_3}{\underset{\mid}{C}}}\!\!\nearrow_{\!\!5}$<br><br>$R_1$ is $-COOCH_2CH_2NHCON\overset{CH_2CH_2OH}{\underset{CH_2CH_2OH}{<}}$ |

TABLE II-continued

| Polymer Number | Vinyl Polymers* |
|---|---|
| 5 (Example 13) | $\text{+CH}_2-\underset{\underset{\text{COOC}_4\text{H}_9}{|}}{\overset{\overset{\text{CH}_3}{|}}{\text{C}}}\text{)}_{95}-\text{(CH}_2-\underset{\underset{R_1}{|}}{\overset{\overset{\text{CH}_3}{|}}{\text{C}}}\text{)}_5$ |
| | $R_1$ is $-\text{COOCH}_2\text{CH}_2\text{NHCON}\underset{\diagdown}{\overset{\diagup}{}}\begin{array}{l}\text{CH}_2\text{CH}_2\text{OH}\\ \text{CH}_2\text{CH}_2\text{OH}\end{array}$ |
| 6 (Example 14) | $\text{+CH}_2-\underset{\underset{\text{COOCH}_3}{|}}{\text{CH})}_{90}-\text{(CH}_2-\underset{\underset{R_1}{|}}{\overset{\overset{\text{CH}_3}{|}}{\text{C}}}\text{)}_{10}$ |
| | $R_1$ is $-\text{COOCH}_2\text{CH}_2\text{NHCON}\underset{\diagdown}{\overset{\diagup}{}}\begin{array}{l}\text{CH}_2\text{CH}_2\text{OH}\\ \text{CH}_2\text{CH}_2\text{OH}\end{array}$ |

EXAMPLE 15

Preparation of Benzene-1-(1-N′,N′-bis(2-hydroxyethyl)ureido-1-methylethyl)-3-(1-methylethenyl)

Twenty-one grams of diethanolmine (0.2M.) were mixed with 9.3 mg of p-methoxyphenol and heated under nitrogen to about 65° C. With moderate stirring, 40.3 g of α,α-dimethylmeta-isopropenylbenzyl isocyanato (m-TMI) (0.2M.) were slowly added over a period of 30 minutes, maintaining the temperatures at 65°-70° C. The content was allowed to stir for additional 90 minutes, and then discharged while still warm. The product showed no NCO absorption (IR spectrum), and the purity was found to be about 96% (GC essay). It was ground into fine powder with melting range of 75°-80° C. The reaction is shown below:

$$\text{CH}_2=\underset{\underset{}{|}}{\overset{\overset{\text{CH}_3}{|}}{\text{C}}}\text{-}\bigcirc\text{-}\underset{\underset{\text{CH}_3}{|}}{\overset{\overset{\text{CH}_3}{|}}{\text{C}}}\text{-NCO} + \text{NH(CH}_2\text{CH}_2\text{OH)}_2 \longrightarrow$$

(m-TMI)

$$\text{CH}_2=\text{CH}_2\underset{\underset{}{|}}{\overset{\overset{\text{CH}_3}{|}}{\text{C}}}\text{-}\bigcirc\text{-}\underset{\underset{\text{CH}_3}{|}}{\overset{\overset{\text{CH}_3}{|}}{\text{C}}}\text{-NHCON(CH}_2\text{CH}_2\text{OH)}_2$$

EXAMPLE 16

Preparation of an Unsaturated Polyurethane Containing Diol of Example 15

In a 2-liter flask were charged 83 g of Tone 0210 (MW 830, a polycaprolactone diol supplied by Union Carbide), 30.6 g of monomer as obtained from Example 15 (0.1M.), and 50 mg of p-methoxyphenol. The contents were heated to 30° C. under N2 and a solution consisting of 131 g of RMDI (methylene dicyclohexyl diisocyanate, 0.5M.), 4 ml of 2% DBTDL (dibutyl tin dilaurate, in toluene) and 250 g of THF is dropped in over a period of 30 minutes. The temperature was raised to 60° C. and stirring continued for 4 hours. Then 27.9 g of 1,4-butanediol (0.31M.), dissolved in 150 g of THF, were added over a 20 minute period. Stirring continued for 2 hours at 60° C. Additional 4 ml of 2% DBTDL were added and the reaction continued for several hours until no NCO was detected by IR spectrum. The product was then cooled and diluted with 690 g of THF to obtain a 20% polymer solution.

A small amount of polymer solution obtained in this example was mixed with about an equal amount of styrene monomer with the free radical initiator, AIBN (azodiisobutyronitrile), and heated in an aluminum cup at 90°-95° C. for about 30 minutes. The film was found to be insoluble in THF, indicating curing had occurred through the unsaturated groups of the polymer and styrene.

The invention has been described in detail with particular reference to preferred embodiments thereof, but it will be understood that variations and modifications can be effected within the spirit and scope of the invention.

What is claimed is:

1. A compound having the structure $$\text{CH}_2=\underset{\underset{}{|}}{\overset{\overset{R}{|}}{\text{C}}}\text{-A-R}_2\text{-NHCON(R}_3\text{OH)}_2;$$

wherein

A represents arylene or carboxyl;

R represents H or $CH_3$; and $R_2$ and $R_3$, each independently, represents alkylene of 2 to 7 carbon atoms.

2. The compound of claim 1 having the structure $$\text{CH}_2=\underset{\underset{}{|}}{\overset{\overset{\text{CH}_3}{|}}{\text{C}}}\text{-A-R}_2\text{-NHCON}\underset{\diagdown}{\overset{\diagup}{}}\begin{array}{l}\text{CH}_2\underset{\underset{R_4}{|}}{\text{CHOH}}\\ \text{CH}_2\underset{\underset{R_4}{|}}{\text{CHOH}}\end{array};$$

wherein

A represents carboxyl or phenylene;

$R_2$ represents ethylene or isopropylene; and $R_4$ represents H or $CH_3$.

3. The compound of claim 1 selected from the group consisting of 2-[N′,N′-bis(2-hydroxyethyl)ureido]ethyl methacrylate; 2-[N′,N′-bis(1-hydroxy-2-propyl)ureido]ethyl methacrylate and Benzene-1-(1-N′,N′-bis(2-hydroxyethyl)ureido-1-methylethyl)-3-(1-methylethenyl).

4. A method for making a compound having the structure $$\text{CH}_2=\underset{\underset{}{|}}{\overset{\overset{R}{|}}{\text{C}}}\text{-A-R}_2\text{-NHCON(R}_3\text{OH)}_2;$$

wherein

A represents arylene or carboxyl;

R represents H or $CH_3$; and $R_2$ and $R_3$, each independently, represents alkylene of 2 to 7 carbon atoms comprising the step of reacting an isocyanatoalkyl acrylate or an isocyanatoarylvinyl with a dialkanol amine at a temperature of 10° to 35° C., in (a) an inert atmosphere, (b) the presence of a free-radical inhibitor and (c) the presence of a urethane catalyst.

5. A polyurethane comprising recurring diol derived units from a compound having the structure

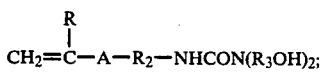

wherein

A represents arylene or carboxyl;

R represents H or CH$_3$; and

R$_2$ and R$_3$, each independently, represents alkylene of 2 to 7 carbon atoms.

6. The polyurethane of claim 5 having recurring units derived from the compound of claim 1 having the structure

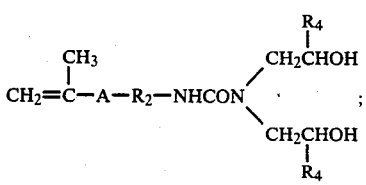

wherein

A represents carboxyl or phenylene; and

R$_2$ represents ethylene or isopropylene; and

R$_4$ represents H or CH$_3$.

7. The polyurethane of claim 6 comprising recurring diol derived units from monomers having the structure

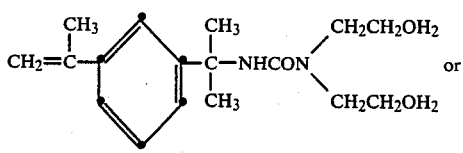

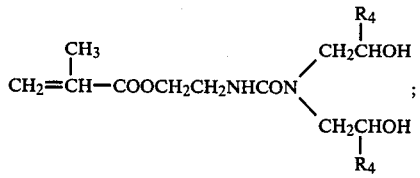

wherein

R$_4$ represents H or CH$_3$.

8. The polyurethane of claim 5 comprising recurring diol derived units from the group consisting of 2-[N',N'-bis(2-hydroxyethyl)ureido]ethyl methacrylate; 2-[N',N'-bis(1-hydroxy-2-propyl)ureido]ethyl methacrylate and Benzene-1-(1-N',N'-bis(2-hydroxyethyl)ureido-1-methylethyl)-3-(1-methylethenyl).

9. The polyurethane of claim 5 comprising from 0.5 to 50 mole percent of such recurring diol derived units.

10. A polyester comprising recurring diol derived units from a compound having the structure:

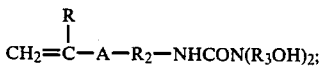

wherein

A represents arylene or carboxyl;

R represents H or CH$_3$; and

R$_2$ and R$_3$, each independently, represents alkylene of 2 to 7 carbon atoms.

11. The polyester of claim 10 comprising recurring diol derived units from the compound of claim 1 having the structure

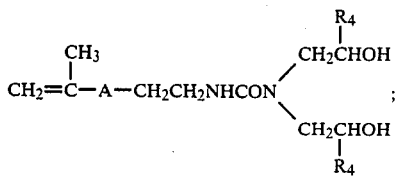

wherein

A represents carboxyl or phenylene; and

R$_4$ represents H or CH$_3$.

12. The polyester of claim 10 comprising diol derived recurring units from monomers having the structure

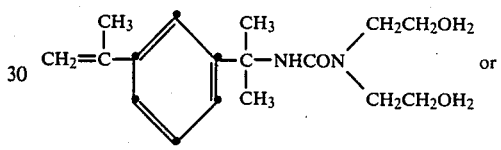

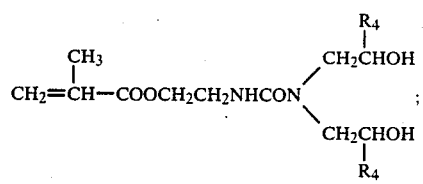

wherein

R$_4$ represents H or CH$_3$.

13. The polyester of claim 10 comprising diol derived units from the group consisting of 2-[N',N'-bis(2-hydroxyethyl)ureido]ethyl methacrylate; 2-[N',N'-bis(1-hydroxy-2-propyl)ureido]ethyl methacrylate and Benzene-1-(1-N',N'-bis(2-hydroxyethyl)ureido-1-methylethyl)-3-(1-methylethenyl).

14. A vinyl polymer comprising recurring units derived from a compound having the structure

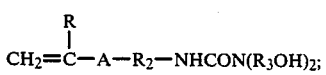

wherein

A represents arylene or carboxyl;

R represents H or CH$_3$; and

R$_2$ and R$_3$, each independently, represents alkylene of 2 to 7 carbon atoms.

15. The vinyl polymer of claim 14 comprising recurring units derived from the compound of claim 1 having the structure

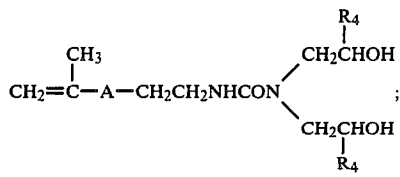

wherein

A represents carboxyl or phenylene; and $R_4$ represents H or $CH_3$.

16. The vinyl polymer of claim 14 comprising recurring units derived from monomers having the structure

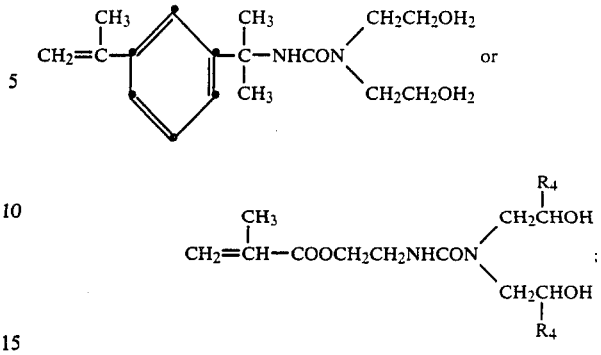

wherein
$R_4$ represents H or $CH_3$.

17. The vinyl polymer of claim 16 comprising recurring units derived from the group consisting of 2-[N',N'-bis(2-hydroxyethyl)ureido]ethyl methacrylate; 2-[N'N'-bis(1-hydroxy-2-propyl)ureido]ethyl methacrylate and Benzene-1-(1-N',N'-bis(2-hydroxyethyl)ureido-1-methylethyl)-3-(1-methylethenyl).

* * * * *